US012690836B2

(12) United States Patent
Yoda et al.

(10) Patent No.: US 12,690,836 B2
(45) Date of Patent: Jul. 28, 2026

(54) THICKNESS CALCULATION METHOD, CALCULATION DEVICE, AND PROGRAM

(71) Applicant: SEIKO EPSON CORPORATION, Tokyo (JP)

(72) Inventors: Kaori Yoda, Shiojiri (JP); Ryoichi Shimura, Azumino (JP); Mio Sasaki, Shiojiri (JP)

(73) Assignee: SEIKO EPSON CORPORATION, Tokyo (JP)

( * ) Notice: Subject to any disclaimer, the term of this patent is extended or adjusted under 35 U.S.C. 154(b) by 0 days.

(21) Appl. No.: 18/898,777

(22) Filed: Sep. 27, 2024

(65) Prior Publication Data

US 2025/0099071 A1 Mar. 27, 2025

(30) Foreign Application Priority Data

Sep. 27, 2023 (JP) ................................. 2023-164708

(51) Int. Cl.
*A61B 8/08* (2006.01)
(52) U.S. Cl.
CPC .................................. *A61B 8/0858* (2013.01)
(58) Field of Classification Search
None
See application file for complete search history.

(56) References Cited

U.S. PATENT DOCUMENTS

2021/0259656 A1* 8/2021 Iura ........................ G06N 3/045

FOREIGN PATENT DOCUMENTS

JP H04231945 A * 8/1992

OTHER PUBLICATIONS

Neumann et al., "Data Descriptor: reference data on thickness and mechanics of tissue layers and anthropometry of musculoskeletal extremities". Scientific Data 5:18093. Sep. 2018. (Year: 2018).*
Woldemariam et al., "Measuring abdominal visceral fat thickness with sonography: a methodologic approach". Journal of Diagnostic Medical Sonography. 2018 vol. 34(2) 91-96. (Year: 2018).*

* cited by examiner

*Primary Examiner* — Yi-Shan Yang
(74) *Attorney, Agent, or Firm* — CHIP LAW GROUP

(57) ABSTRACT

A thickness calculation method for calculating a thickness of a tissue in a living body by a computer, a processor of the computer performs acquiring received data based on a reception signal of an ultrasonic wave for a target living body, classifying the target living body into one of a first attribute and a second attribute based on the acquired received data, (i) calculating a thickness of a target tissue by inputting the acquired received data into a first training model, when the target living body is classified into the first attribute, and calculating the thickness of the target tissue by inputting the acquired received data into a second training model, when the target living body is classified into the second attribute.

8 Claims, 8 Drawing Sheets

FIG. 8

THICKNESS CALCULATION METHOD, CALCULATION DEVICE, AND PROGRAM

The present application is based on, and claims priority from JP Application Serial Number 2023-164708, filed Sep. 27, 2023, the disclosure of which is hereby incorporated by reference herein in its entirety.

BACKGROUND

1. Technical Field

The present disclosure relates to a thickness calculation method, a calculation device, and a program.

2. Related Art

In JP-A-H4-231945, it is disclosed that a fat layer is measured based on a reception signal obtained by transmitting ultrasonic waves to a living body.

The reception signal obtained by transmitting the ultrasonic wave to the living body is affected not only by the thickness of the tissue to be measured but also by other physical characteristics of the living body. There is a demand for a technique for measuring the thickness of tissue of a living body with higher accuracy using a reception signal regardless of the physical characteristics of the living body.

SUMMARY

According to a first aspect of the present disclosure, there is provided a thickness calculation method for calculating a thickness of the tissue in a living body by a computer. In this calculation method, the computer has a processor or a plurality of processors, and the processor or the plurality of processors performs a data acquisition step that acquires received data based on a reception signal output when an ultrasonic wave transmitted from an ultrasonic probe is reflected within a living body of a target and is received by the ultrasonic probe, a living body attribute classification step that classifies the living body of the target into one of a first attribute relating to a physique of the living body and a second attribute relating to the physique based on target received data, which is the received data acquired in the data acquisition step, and a thickness calculating step of (i) when the target living body is classified into the first attribute in the living body attribute classification step, calculating thickness of tissue at a predetermined part of the target living body by inputting the target received data into a first training model that learned in advance and (ii) when the target living body is classified into the second attribute in the living body attribute classification step, calculating the thickness of the tissue by inputting the target received data into a second training model that learned in advance. The first training model learned in advance using, as teaching data, first sample data, which is the received data for a biological sample having the first attribute, and a thickness label related to the thickness of the tissue associated with the first sample data. The second training model learned in advance using, as teaching data, second sample data that is the received data on the biological sample having the second attribute and the thickness label associated with the second sample data.

According to a second aspect of the present disclosure, there is provided a calculation device for calculating thickness of tissue in a living body. The calculation device includes a storage device that stores a first training model learned in advance and a second training model learned in advance, and a processor or a plurality of processors. The processor or the plurality of processors performs a data acquisition step that acquires received data based on a reception signal output when an ultrasonic wave transmitted from an ultrasonic probe is reflected within a living body of a target and is received by the ultrasonic probe, a living body attribute classification step that classifies the living body of the target into one of a first attribute relating to a physique of the living body and a second attribute relating to the physique based on target received data, which is the received data acquired in the data acquisition step, and a thickness calculating step of (i) when the target living body is classified into the first attribute in the living body attribute classification step, calculating thickness of tissue at a predetermined part of the target living body by inputting the target received data into a first training model and (ii) when the target living body is classified into the second attribute in the living body attribute classification step, calculating the thickness of the tissue by inputting the target received data into a second training model. The first training model learned in advance using, as teaching data, first sample data, which is the received data for a biological sample having the first attribute, and a label related to the thickness of the tissue associated with the first sample data. The second training model learned in advance using, as teaching data, second sample data, which is the received data on the biological sample having the second attribute and the label associated with the second sample data.

According to a third aspect of the present disclosure, there is provided a program for causing a computer to realize a function of calculating a thickness of the tissue in a living body. The program causes the computer to realize a function of executing a data acquisition step of acquiring received data based on a reception signal output when an ultrasonic wave transmitted from an ultrasonic probe is reflected in a living body of a target and is received by the ultrasonic probe, a function of executing a living body attribute classification step of classifying the target biological object into one of a first attribute relating to a physique of the biological object and a second attribute relating to the physique based on target received data, which is the data acquired in the data acquisition step, and a function of a thickness calculating step of (i) when the target living body is classified into the first attribute in the living body attribute classification step, calculating thickness of tissue at a predetermined part of the target living body by inputting the target received data into a first training model that learned in advance and (ii) when the target living body is classified into the second attribute in the living body attribute classification step, calculating the thickness of the tissue by inputting the target received data into a second training model that learned in advance. The first training model learned in advance using, as teaching data, first sample data, which is the received data for a biological sample having attribute, and a label related to the thickness of the tissue associated with the first sample data. The second training model learned in advance using, as teaching data, second sample data, which is the received data on the biological sample having the second attribute and the label associated with the second sample data.

BRIEF DESCRIPTION OF THE DRAWINGS

FIG. 8 is a diagram illustrating an example of a segmentation result.

DESCRIPTION OF EMBODIMENTS

A. First Embodiment

Figure 1:
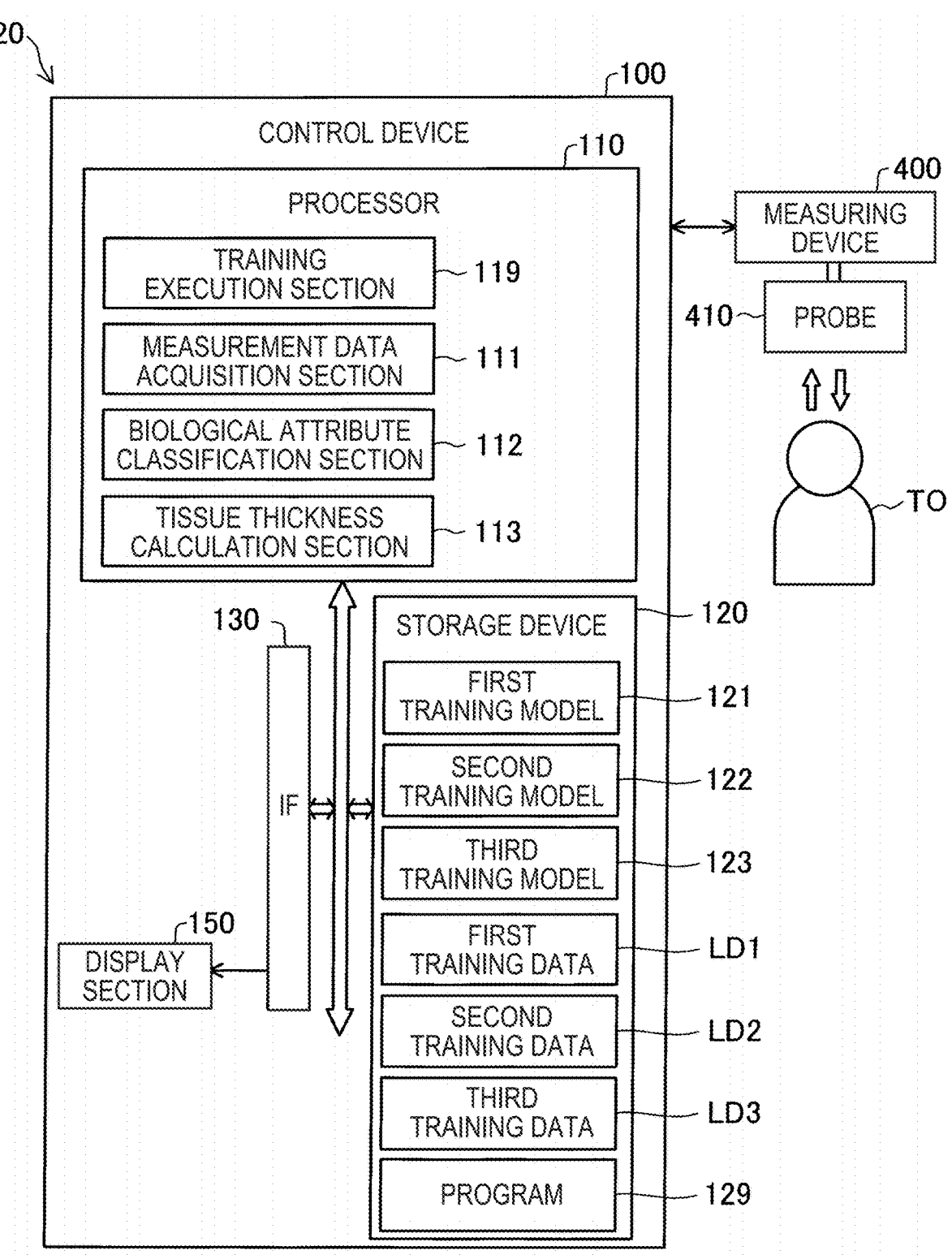
FIG. 1 is a diagram showing a schematic configuration of a calculation device.

FIG. 1 is a diagram showing a schematic configuration of a calculation device 20 in a first embodiment. The calculation device 20 is a device that calculates the thickness of tissue in a target living body TO by using ultrasonic waves. The target living body TO is, for example, a person such as a user or a subject who uses the calculation device 20. Hereinafter, the tissue to be a target of thickness measurement is also referred to as a target tissue. The target tissue may be the tissue in any predetermined body portion, for example, a tissue in the abdomen or thigh. The target tissue may be any type of tissue, for example, a muscle layer or a fat layer. The target tissue in the present embodiment is a layer of skeletal muscle. Specifically, the target tissue is the rectus abdominis muscle.

The calculation device 20 includes a control device 100 and a measuring device 400 having an ultrasonic probe 410. The control device 100 includes one or a plurality of processors 110, a storage device 120, an interface circuit 130, and a display section 150 coupled to the interface circuit 130. The control device 100 is, for example, a personal computer. The storage device 120 includes, for example, a ROM and a RAM. The display section 150 displays various kinds of information. The display section 150 is, for example, a liquid crystal display monitor. The control device 100 and the measuring device 400 can perform data communication with each other by wired or wireless lines.

Figure 2:
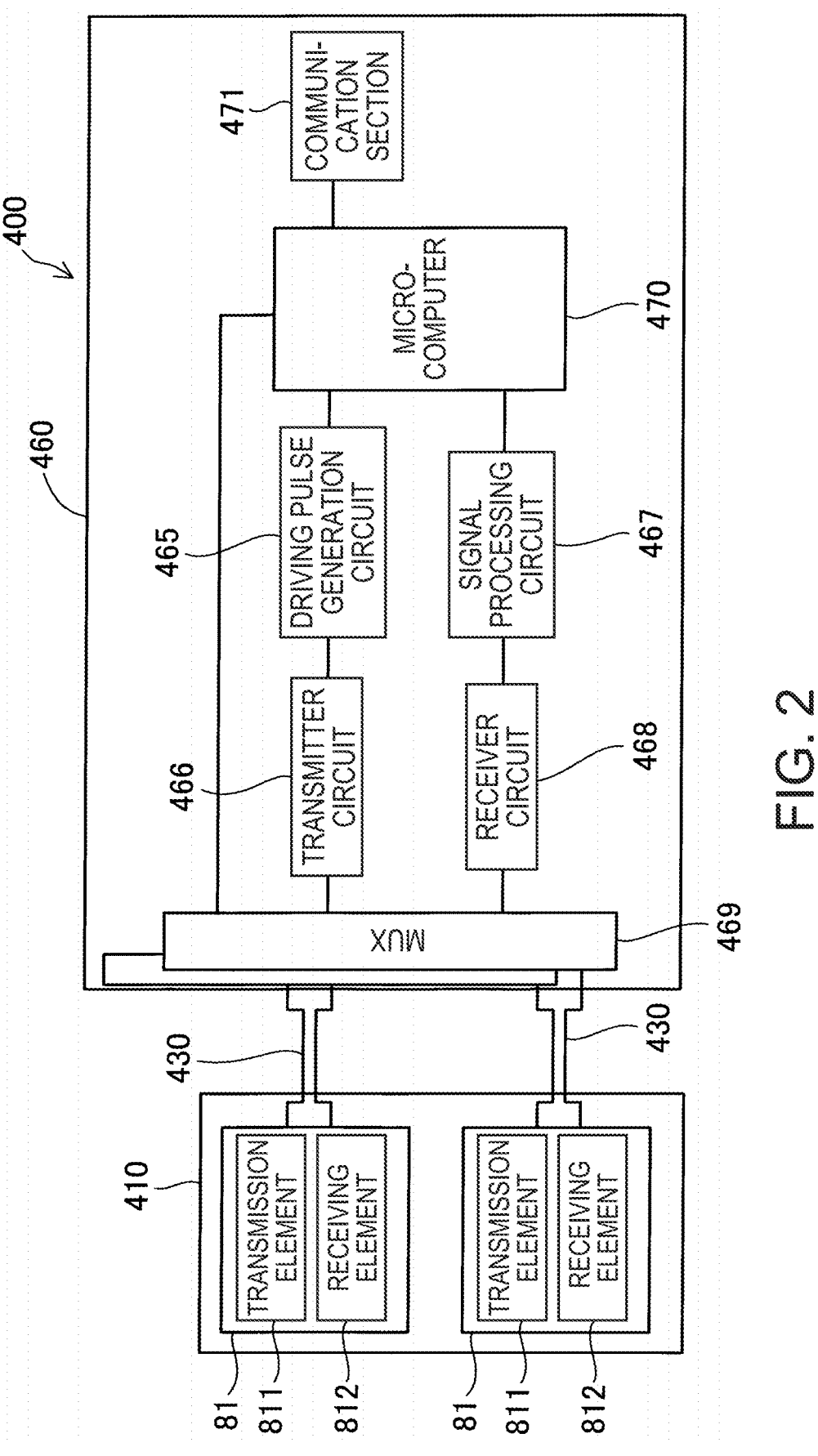
FIG. 2 is a diagram for explaining a measuring device.

FIG. 2 is a diagram for explaining the measuring device 400. The measuring device 400 is configured as an ultrasonic transmitting and receiving device that transmits ultrasonic waves to a living body and receives ultrasonic waves reflected by the living body. The measuring device 400 includes the ultrasonic probe 410 having the ultrasonic element 81 for transmitting and receiving ultrasonic waves, and a control section 460 for executing control and signal processing of the ultrasonic probe 410. The ultrasonic probe 410 and the control section 460 are electrically coupled to each other by a wiring 430.

The ultrasonic probe 410 includes one or more ultrasonic element 81. The ultrasonic element 81 includes an ultrasonic transmission element 811 and an ultrasonic receiving element 812. In the present embodiment, one ultrasonic element 81 has a function as the transmission element 811 and a function as the receiving element 812. The transmission element 811 transmits ultrasonic waves toward a target tissue. While traveling in the living body along the thickness direction of the target tissue, the transmitted ultrasonic wave is reflected by the target tissue in the living body TO. By this, the transmitted ultrasonic wave becomes a reflected wave, and it is received by the receiving element 812. When the reflected wave is received by the receiving element 812, a reception signal is output from the receiving element 812. When the ultrasonic probe 410 includes a plurality of ultrasonic elements 81, the ultrasonic elements 81 are arranged, for example, in a line at equal intervals on a plate-shaped base member. The ultrasonic probe 410 is used in a state where the ultrasonic element 81 is brought close to the surface of the living body. Specifically, the ultrasonic probe 410 is used in a state of being pressed against or fixed to the surface of the living body so that the ultrasonic element 81 approaches the surface of the living body. Although two ultrasonic elements 81 are shown in FIG. 2, the number of ultrasonic elements 81 may be one, or three or more.

The control section 460 generates received data based on the reception signal output from each ultrasonic element 81. In the present embodiment, the control section 460 generates a so-called B-mode image as received data. In the B-mode image, a difference in the intensity of the reflected wave is expressed as a difference in brightness in the image. A part including at least a target tissue is represented in the B-mode image. The reception signal for obtaining such a B-mode image is acquired, for example, by using the plurality of ultrasonic elements 81 or by scanning one or the plurality of ultrasonic elements 81 along the body surface in a direction intersecting the thickness direction. Hereinafter, the part including the target tissue is also referred to as a target site. Specifically, the target site in the present embodiment includes parts from a muscle layer, which is the target tissue, to a part on the body surface located near the muscle layer.

The control section 460 includes a driving pulse generation circuit 465, a transmitter circuit 466, a signal processing circuit 467, a receiving circuit 468, a multiplexer 469, a microcomputer 470, and a communication section 471. The driving pulse generation circuit 465 generates a pattern of a predetermined drive frequency and wave number at the time of transmission of an ultrasonic wave. The transmitter circuit 466 outputs a transmission waveform of a predetermined drive voltage according to the generated pattern. Each of the transmission elements 811 transmits the transmitted waveform output from the transmitter circuit 466 toward the measurement target site as an ultrasonic wave. The receiving circuit 468 amplifies a reception signal received by each receiving element 812. The signal processing circuit 467 generates a so-called A-mode image by performing envelope processing, LOG compression processing, and the like on the reception signal amplified by the receiving circuit 468. The microcomputer 470 is configured to sequentially switch each transmitting and receiving operation of each ultrasonic element 81 by the multiplexer 469. In other words, each ultrasonic element 81 is configured to sequentially receive each reception signal.

The ultrasonic waves are hardly reflected from tissue such as a fat layer or a muscle layer, whereas they are more likely to be reflected in a fascia located at the boundary between tissues. As used herein, the term "fascia" refers to a thin connective tissue that covers and protects various tissues, such as muscles, bones, internal organs, nerves, and blood vessels. By using this property of the ultrasonic wave, the position of the fascia on one side of the target tissue and the position of the fascia on the other side of the target tissue in the thickness direction of the target tissue can be based on the received data, and the position of the first end and the position of the second end in the thickness direction of the target tissue can be identified. The distance in the thickness direction between the position of the first end and the position of the second end specified in this way corresponds to the thickness of the target tissue.

In addition to the fascia, the ultrasonic wave is more likely to be reflected by, for example, intramuscular fat, which is fat within a muscle layer, and cellulite within a fat layer, as compared to other parts in each tissue. As a result, the received data may include, as noise, a feature amount related to the position of intramuscular fat or cellulite in addition to a feature amount related to the position of the fascia. Such noise tends to cause the position of the fascia to be erroneously identified when the position of the fascia is identified using the received data. The reflection intensity of the ultrasonic wave in the living body also changes depending on, for example, the state or degree of intramuscular fat or cellulite. The state or degree of such intramuscular fat or cellulite in a living body correlates with physical characteristics such as the physique of the living body. Specifically, for example, in the case of a person who tends to be obese due to lack of exercise, the amount of intramuscular fat or cellulite tends to be larger. For example, the distribution of intramuscular fat and cellulite varies depending on the presence or absence of exercise habit. In other words, the received data may be affected by the physical characteristics of the target living body TO.

The storage device 120 illustrated in FIG. 1 stores a first training model 121, a second training model 122, a third training model 123, first training data LD1, second training data LD2, third training data LD3, and a program 129. The processor 110 realizes various functions including functions as a measurement data acquisition section 111, a biological attribute classification section 112, the tissue thickness calculation section 113, and a training execution section 119 by executing the program 129 stored in the storage device 120. Each of the measurement data acquisition section 111, the biological attribute classification section 112, and the tissue thickness calculation section 113 is a functional unit used for the measurement processing described below. The training execution section 119 is a functional unit used for a training process (to be described later). Hereinafter, in a case where the first training model 121, the second training model 122, and the third training model 123 are not distinguished from each other, each is simply referred to as a training model. The first training model 121 and the second training model 122 are training models used in a thickness calculating step (described later) and are also referred to as calculation models. The third training model 123 is a training model used in the living body attribute classification step (described later) and is also referred to as a classification model. In present each embodiment, training model is a convolutional neural network that has been trained by supervised learning. Hereinafter, the convolutional neural network is also simply referred to as a CNN. Details of the first training data LD1 to the third training data LD3 will be described later.

The measurement data acquisition section 111 executes a data acquisition step. The data acquisition step is a process of acquiring received data output from the ultrasonic probe 410 of the measuring device 400. The measurement data acquisition section 111 stores the received data acquired in the data acquisition step in storage device 120. Hereinafter, the received data acquired in the data acquisition step is also referred to as target received data. It can also be said that the target received data is data used for measuring the thickness of the target tissue with respect to the target living body TO.

The biological attribute classification section 112 executes a living body attribute classification step. The living body attribute classification step is a step of classifying the target living body TO into one of the first attribute and the second attribute based on the target received data acquired by the measurement data acquisition section 111. Each of the first attribute and the second attribute is an attribute related to the physique of the living body. The first attribute in the present embodiment represents an attribute showing a slimmer physique compared to the second attribute. Hereinafter, classifying the target living body TO into one of the first attribute and the second attribute is also simply referred to as "classifying the target living body TO".

In present embodiment, the first attribute and the second attribute are classified according to the size of physique parameter, which is a parameter related to the physique of the living body. The physique parameter is preferably a parameter representing at least one of fat thickness, body fat percentage, and Body Mass Index (BMI). In the present embodiment, the physique parameter is a parameter representing fat thickness. Specifically, the fat thickness is the thickness of a fat layer, which is a layer of subcutaneous fat located on the epidermis side of a muscle layer, which is the target tissue. In other words, the fat thickness in present embodiment is the thickness of the fat layer located on the skin side of the rectus abdominis muscle. The first attribute in present embodiment is an attribute that the fat thickness is equal to or less than a predetermined reference thickness. The second attribute is an attribute indicating that the fat thickness is larger than the reference thickness.

In the present embodiment, the biological attribute classification section 112 classifies the target living body TO using the third training model 123 described above in the living body attribute classification step. As will be described later, the third training model 123 is a learned model different from the first training model 121 and the second training model 122.

The tissue thickness calculation section 113 performs a thickness calculating step to calculate the thickness of the target tissue. In the thickness calculating step, the tissue thickness calculation section 113 executes one of a first process or a second process according to the attribute of the target living body TO classified in the living body attribute classification step. The first process is executed when the target living body TO is classified into the first attribute in the living body attribute classification step. The first process is a process of inputting the target received data into the first training model 121 and calculating the thickness of the target tissue for the living body TO of the target. The second process is executed when the target living body TO is classified into the second attribute in the living body attribute classification step. The second process is a process of inputting the target received data into the second training model 122 and calculating the thickness of the target tissue for the target living body TO.

Figure 3:
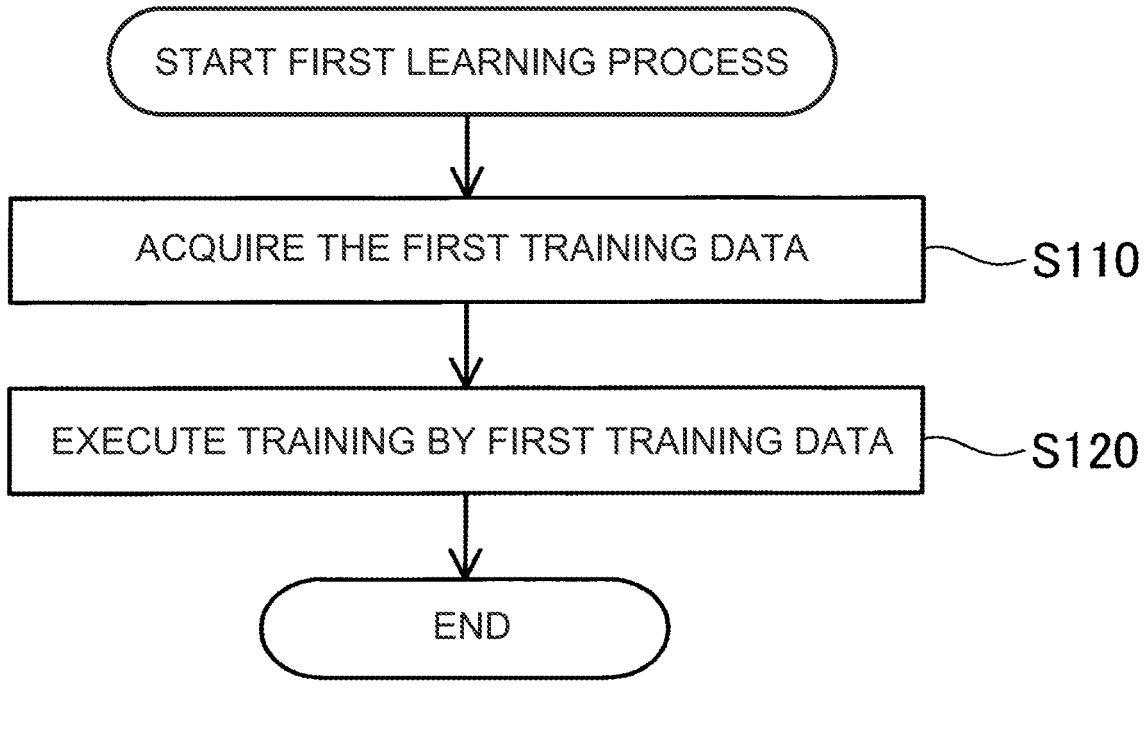
FIG. 3 is a flowchart of a first training process.

FIG. 3 is a flowchart of the first training process executed in the present embodiment. The first training process is a process for causing the first training model 121 to learn. In the present embodiment, the first training process is executed by the user performing a predetermined operation on the control device 100. The first training process is executed prior to a measurement process (to be described later). Each of the first training process, a second training process, and a third training process (to be described later) represents a method of generating a training model.

In step S110, the training execution section 119 acquires the first training data LD1. The first training data LD1 is a dataset for training the first training model 121. The first training data LD1 includes the first sample data, which is the received data for a first attribute biological sample, and a first thickness label associated with the first sample data. To be more specific, the first training data LD1 includes, as main data, a plurality of first sample datasets having the first thickness label. In the present disclosure, main data means the received data of which the ratio to the total number of received data included in the training data is larger than 50% among the received data included in the training data. The ratio of the number of pieces of main data to the training data for causing the calculation model to train is preferably 70% or more, more preferably 80% or more, and still more preferably 90% or more. In the present embodiment, the first training data LD1 is composed of a plurality of first sample data and first thickness labels associated with each first sample data set. In other words, the ratio of the number of first sample data to the total number of received data included in the first training data LD1 is 100%. In step S110, for example, the first training data LD1 may be acquired from the storage device 120 or may be acquired from an external computer or a storage medium.

Specifically, the first sample data is received data based on the reception signal derived from the biological sample having the first attribute. The biological sample is preferably a living body of the same species as the target living body TO. In the present embodiment, the biological sample is a person. The first sample data is received data for the same tissue as the target tissue. Specifically, the first sample data in the present embodiment is the B-mode image representing a target site including at least the rectus abdominis muscle. The biological sample may or may not include the same person as the target living body TO. The first thickness label is a label related to the thickness of the target tissue of the first sample data having the first thickness label. Hereinafter, the label related to the thickness of the target tissue is also referred to as a thickness label.

Figure 4:
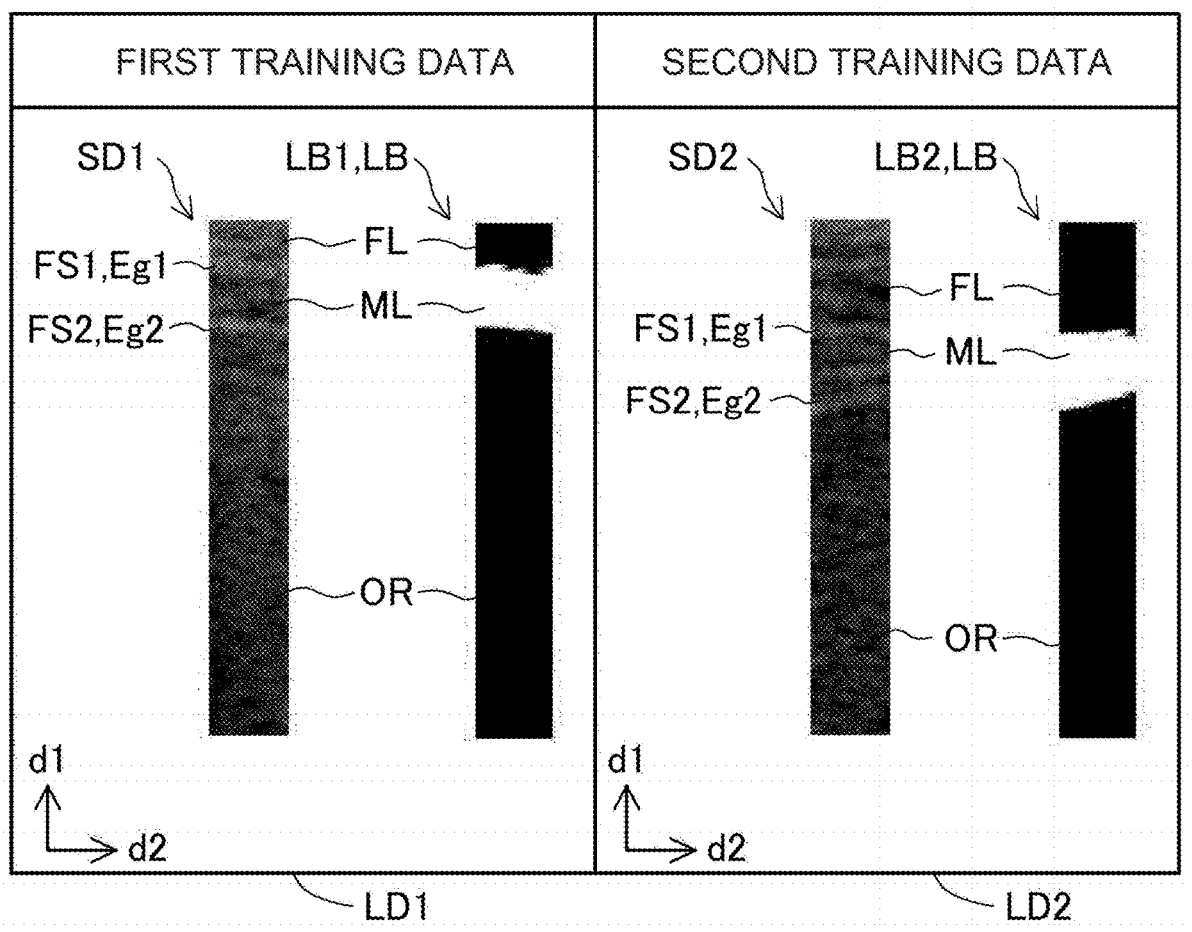
FIG. 4 is a diagram for explaining training data used for the training of each training model.

FIG. 4 is a diagram for explaining training data used for the training of each training model. FIG. 4 shows an example of first sample data SD1 included in first training data LD1 and an example of a first thickness label LB1 associated with the first sample data SD1. FIG. 4 illustrates an example of second sample data SD2 included in second training data LD2 (described later) and an example of a second thickness label LB2 associated with the second sample data SD2. The second thickness label LB2 is a thickness label LB as will be described later. Hereinafter, the first thickness label LB1 and the second thickness label LB2 are also simply referred to as "thickness label LB". Hereinafter, when the first sample data SD1 and the second sample data SD2 are not particularly distinguished from each other, each is simply referred to as sample data.

In FIG. 4, the upper side of the B-mode image, which serves as received data, represents the body surface side in the thickness direction d1 of the body portion including the target tissue. In each B-mode image, the lower side represents the back side in the thickness direction d1 of the body portion including the target tissue. Here, the back side means a side closer to the center of the body of the living body. In each B-mode image, a fat layer FL, a muscle layer ML, and an internal organ OR appear in this order from the top. At the boundary between the fat layer FL and the muscle layer ML, a first fascia FS1, which is a fascia on the epidermis side of the target tissue, appears. At the boundary between the muscle layer ML and the internal organ OR, a second fascia FS2, which is a fascia on the deep side of the target tissue, appears. As described above, the position of the first fascia FS1 represents the position of the first end Eg1 in the thickness direction d1 of the target tissue. The position of the second fascia FS2 represents the position of the second end Eg2 in the thickness direction d1 of the target tissue. Hereinafter, a direction perpendicular to the thickness direction d1 is also referred to as the vertical direction d2.

Each thickness label LB in the present embodiment is a label that indicates whether each region included in the B-mode image of each sample data set associated with the thickness label LB is a region representing a fat layer FL, a muscle layer ML, or an internal organ OR. Specifically, the thickness label LB is, for example, a label indicating whether each pixel in the B-mode image represents one of the fat layer FL, the muscle layer ML, or the internal organ OR. Therefore, the thickness label LB is a label capable of specifying the boundary between the muscle layer ML, which is the target tissue, and other tissues, that is, the first end Eg1 and the second end Eg2. As described above, since the thickness of the target tissue can be calculated by specifying the first end Eg1 and the second end Eg2, the thickness label LB is the label relating to the thickness of the target tissue. FIG. 4 schematically shows the thickness label LB as an image in which the region of the muscle layer ML is masked in order to facilitate understanding of the technique. Specifically, FIG. 4 shows the thickness label LB as an image in which the region of the tissue other than the muscle layer ML is represented in black and the region of the muscle layer ML is represented in white.

In step S120 of FIG. 3, the training execution section 119 executes training of the machine learning model by inputting the first training data LD1 acquired in step S110 to the machine learning model. In other words, in step S120, supervised learning using the first training data LD1 as teaching data is performed. As a result, the learned first training model 121 is generated using the first training data LD1 as the teaching data. In present embodiment, when a B-mode image as received data is input, the first training model 121 is generated as a model for executing segmentation of three classes for the B-mode image. Specifically, the first training model 121 outputs, for example, information indicating any one of the fat layer FL, the muscle layer ML, and the internal organ OR that each pixel in the input B-mode image represents as a result of the segmentation. The training execution section 119 stores the generated first training model 121 in the storage device 120.

Figure 5:
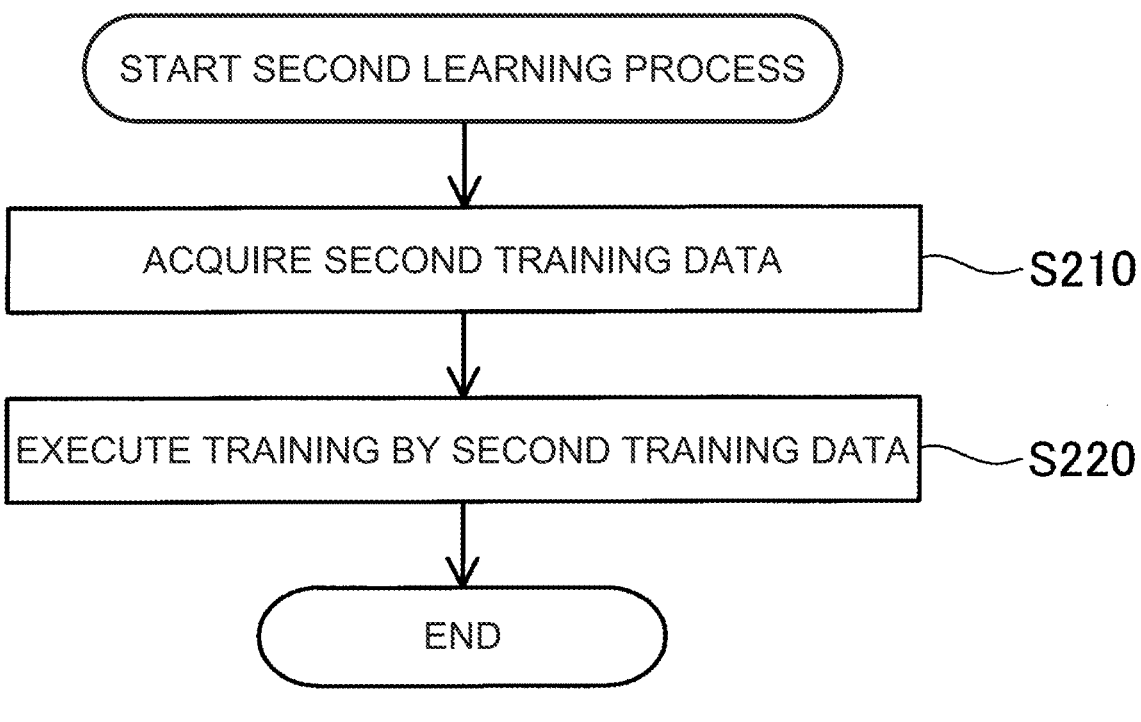
FIG. 5 is a flowchart of a second training process.

FIG. 5 is a flowchart of the second training process executed in the present embodiment. The second training process is a process for causing the second training model 122 to be trained. The second training process is executed prior to the measurement process, similarly to the first training process.

In step S210, the training execution section 119 acquires the second training data LD2. The second training data LD2 is a dataset for training the second training model 122. The second training data LD2 includes the second sample data SD2, which is the received data for a biological sample of the second attribute, and the second thickness label LB2 associated with the second sample data SD2. To be more specific, the second training data LD2 includes, as main data, plural sets of second sample data SD2 with second thickness labels LB2. The second training data LD2 in the present embodiment is composed of plural sets of second sample data SD2 and the second thickness labels LB2 associated with the respective sets of second sample data SD2. In other words, the ratio of the amount of second sample data SD2 to the total amount of received data included in the second training data LD2 is 100%. Specifically, the second sample data SD2 is received data based on a reception signal derived from a biological sample having the second attribute. The second thickness label LB2 is a label relating to the thickness of the target tissue in the second sample data SD2 to which the second thickness label LB2 is assigned. In step S210, the second training data LD2 may be acquired from the storage device 120 or from an external computer or a storage medium.

In step S220, the training execution section 119 executes training of the machine learning model by inputting the second training data LD2 acquired in step S210 into the machine learning model. In other words, in step S220, supervised learning is performed using the second training data LD2 as teaching data. As a result, the learned second training model 122 is generated using the second training data LD2 as the teaching data. In present embodiment, the second training model 122 is generated as a model that executes three classes of segmentation when the received data is input, substantially that same as the first training model 121. The training execution section 119 stores the generated second training model 122 in the storage device 120.

Figure 6:
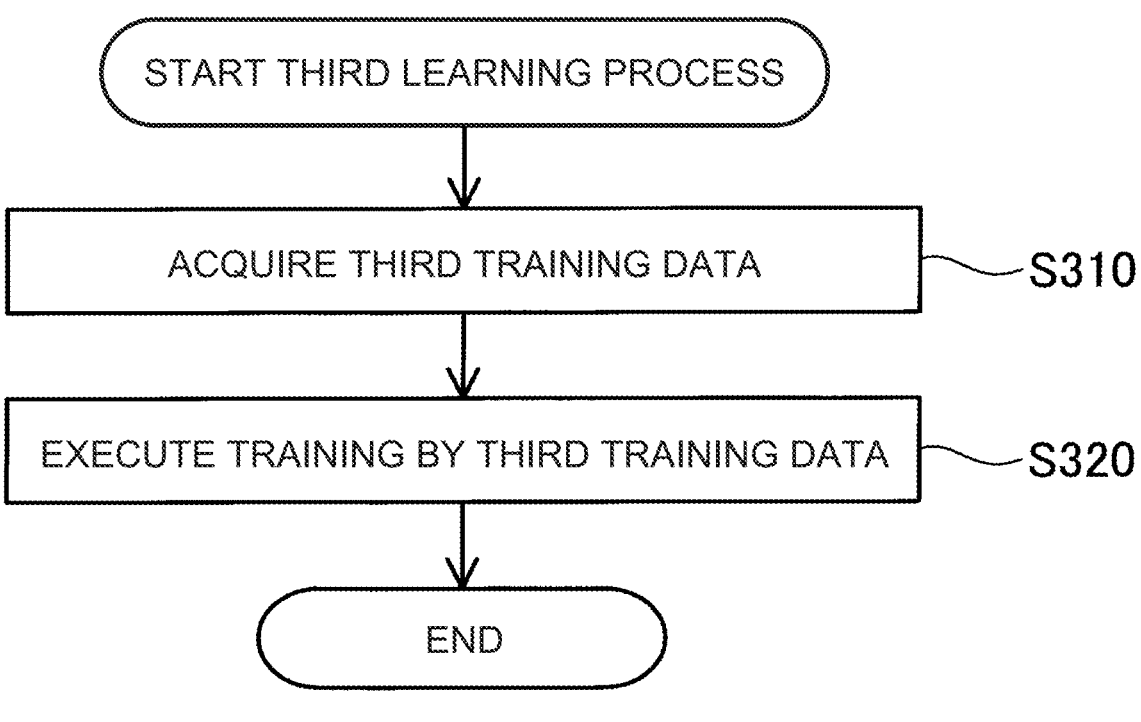
FIG. 6 is a flowchart of a third training process.

FIG. 6 is a flowchart of the third training process executed in the present embodiment. The third training process is a process for causing the third training model 123 to learn. The third training process is executed prior to the measurement process, similarly to the first training process and the second training process.

In step S310, the training execution section 119 acquires the third training data LD3. The third training data LD3 is a dataset for training the third training model 123. The third training data LD3 includes first sample data SD1 and a physique label associated with the first sample data SD1, and second sample data SD2 and a physique label associated with the second sample data SD2. The physique label is a label related to a physique parameter. Specifically, the physique label in the present embodiment is a label indicating whether each region included in the B-mode image is a region of the fat layer FL or a region of the tissue other than the fat layer FL. The physique label is, for example, a label indicating whether each pixel represents the fat layer FL or the tissue other than the fat layer FL in the B-mode image. Therefore, the physique label is a label capable of specifying the boundary between the fat layer FL and the muscle layer ML, that is, the first end Eg1. The thicknesses of the fat layer FL can be calculated by specifying the first end Eg1. In other words, the physique label in the present embodiment is a label related to fat thickness.

As the first sample data SD1 and the second sample data SD2 included in the third training data LD3, the same sample data can be used as the first sample data SD1 included in the first training data LD1 and the second sample data SD2 included in the second learning data LD2. In other words, in the training of the classification model and the training of the calculation model, the sample data to be used may be the same, and only the labels to be assigned to the sample data may be different. In this way, it is possible to reduce time and effort for preparing the sample data, and it is possible to efficiently prepare the teaching data for training the classification model or the calculation model.

In step S320, the training execution section 119 executes the training of the machine learning model by inputting the third training data LD3 acquired in step S310 into the machine learning model. In other words, in step S320, supervised learning using the third training data LD3 as teaching data is executed. As a result, the learned third training model 123 is generated using the third training data LD3 as the teaching data. In the present embodiment, the third training model 123 is generated as a model for performing two-class segmentation when the received data is input. Specifically, the third training model 123 outputs, as a result of the segmentation, for example, information indicating whether each pixel in the input B-mode image is a pixel representing the fat layer FL or tissue other than the fat layer FL. The training execution section 119 stores the generated third training model 123 in the storage device 120.

Figure 7:
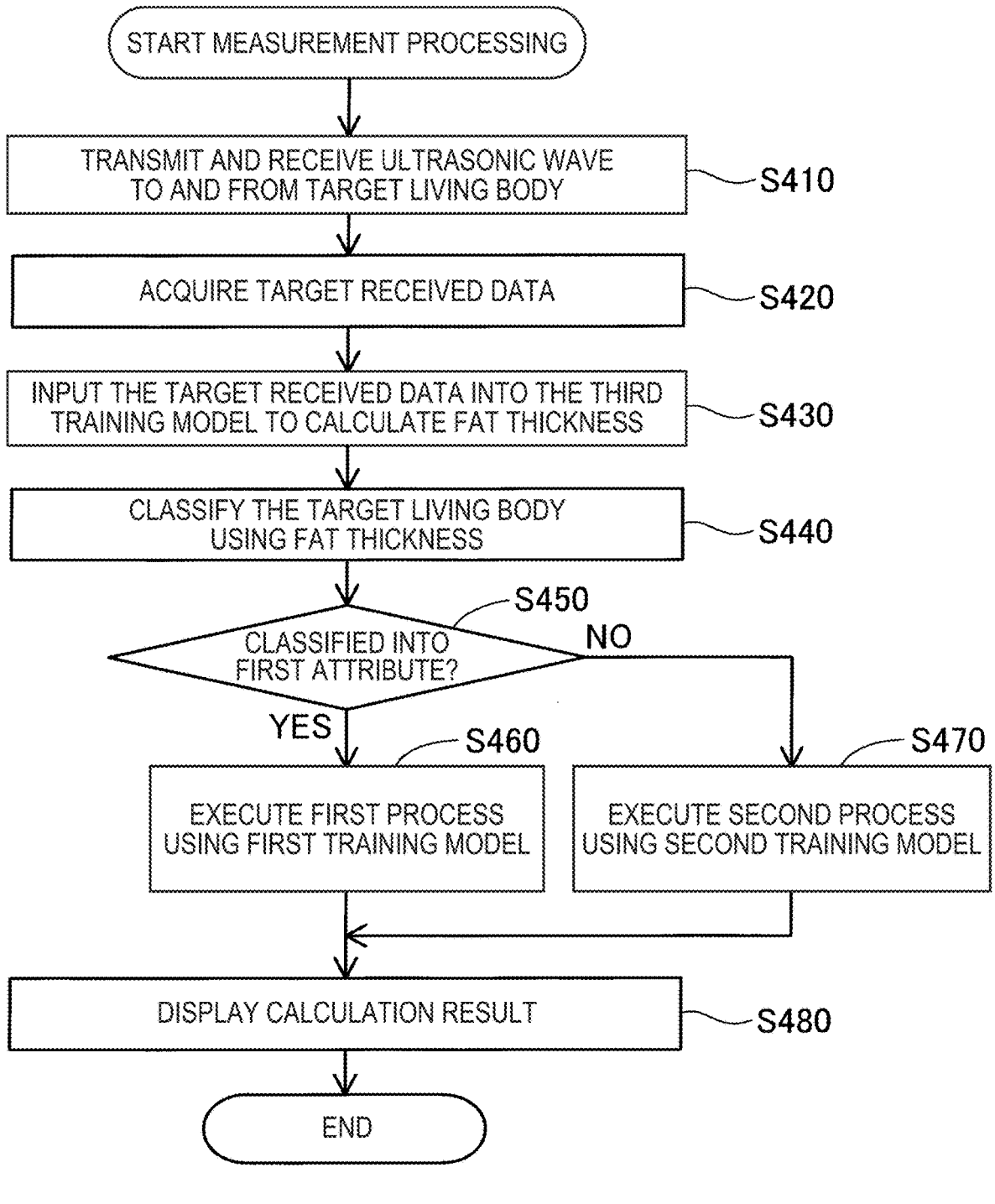
FIG. 7 Is a flowchart of a measurement process.

FIG. 7 is a flowchart of a measurement process for realizing the thickness measurement method in present embodiment. In the present embodiment, the measurement process is executed by a user performing a predetermined operation on the control device 100. In step S410, the control device 100 controls the measuring device 400 and transmits ultrasonic waves from the ultrasonic probe 410 to the target living body TO and causes the ultrasonic probe 410 to receive ultrasonic waves reflected in the target living body TO. As a result, a reception signal is output from the ultrasonic probe 410, and the control section 460 generates received data based on the reception signal.

In step S420, the measurement data acquisition section 111 executes the data acquisition step. To be more specific, in step S420, the measurement data acquisition section 111 acquires the received data generated in step S410. In other words, in step S420, the measurement data acquisition section 111 acquires the target received data.

In step S430 and step S440, the biological attribute classification section 112 executes a living body attribute classification step. In step S430, first, the biological attribute classification section 112 inputs the target received data acquired in step S410 into the third training model 123. As a result, the third training model 123 performs segmentation using the target received data, identifying the position of the first end Eg1 of the target tissue. Next, the biological attribute classification section 112 acquires the fat thickness using the specified first end Eg1. The fat thickness is calculated based on, for example, the distance between the epidermis and the first end Eg1.

In step S440, the biological attribute classification section 112 classifies the target living body TO into one of the first attribute and the second attribute using the fat thickness calculated in step S430. To be specific, in step S440, the biological attribute classification section 112 classifies the target living body TO into the first attribute in a case where the fat thickness calculated in step S430 is equal to or smaller than a reference thickness and classifies the target living body TO into the second attribute in a case where the fat thickness calculated in step S430 is larger than the reference thickness.

In step S450, the tissue thickness calculation section 113 determines whether the target living body TO was classified into the first attribute. In a case where it is determined that the target living body TO was classified into the first attribute in step S450, the tissue thickness calculation section 113 performs the first process in step S460. When it is determined that the target living body TO is classified into the second attribute in step S450, the tissue thickness calculation section 113 executes the second process in step S470.

In step S460, first, the tissue thickness calculation section 113 inputs the target received data into the first training model 121. The target received data is the target received data for the living body having the first attribute. As a result, the first training model 121 performs segmentation using the target received data, identifying the first end Eg1 and the second end Eg2 of the target tissue. Next, the tissue thickness calculation section 113 calculates the thickness of the muscle layer ML, which is the target tissue, using the specified first end Eg1 and second end Eg2. To be specific, the thickness of the target tissue is calculated based on the distances between the first end Eg1 and the second end Eg2.

Step S470 is the same as step S460 except that the target received data is input into the second training model 122 instead of the first training model 121. In other words, the tissue thickness calculation section 113 inputs the target received data for the living body of the second attribute into the second training model 122 and calculates the thickness of the muscle layer ML, which is the target tissue.

Figure 8:
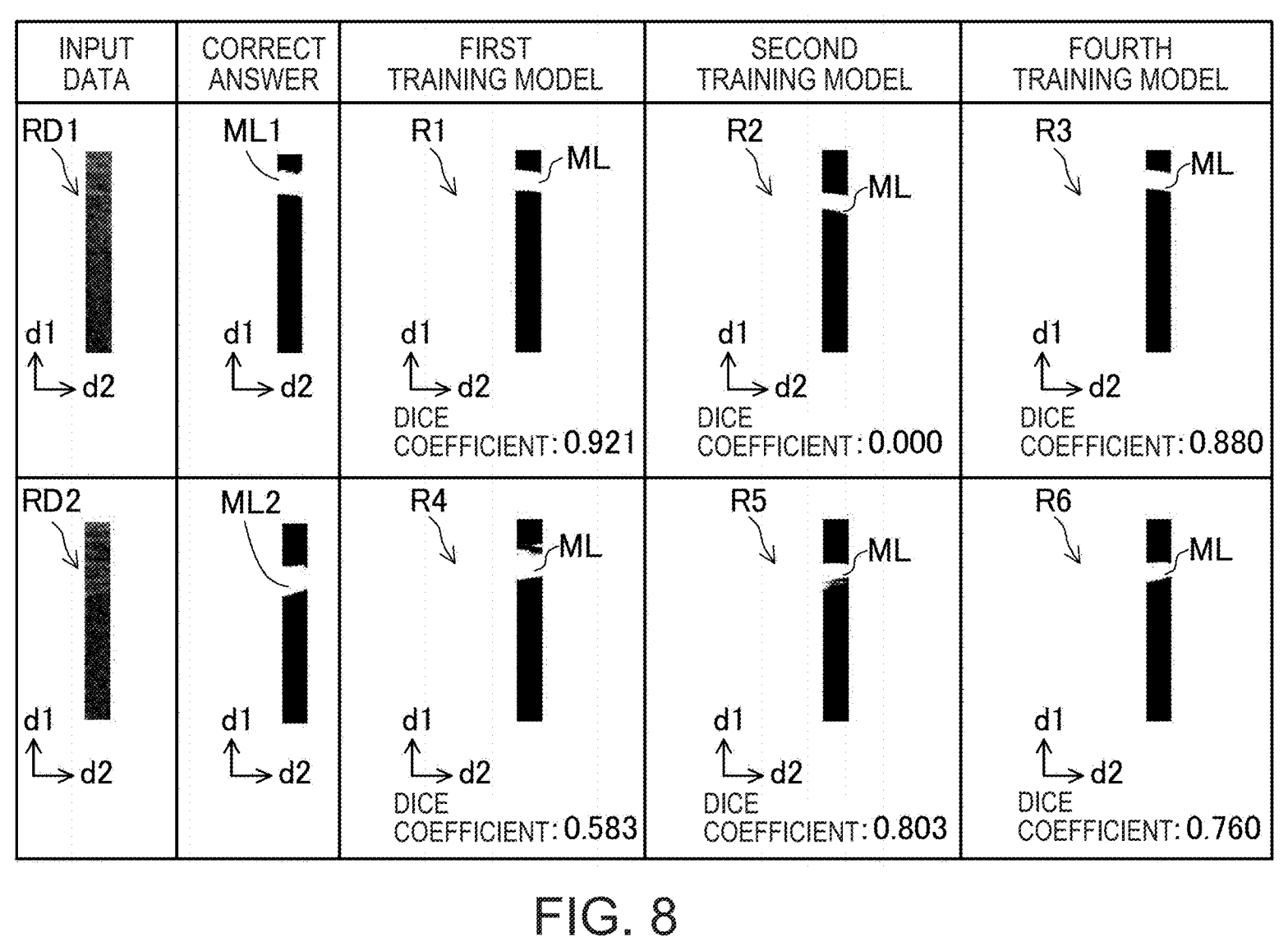

FIG. 8 is a diagram illustrating an example of a segmentation result by the first training model 121 and the second training model 122. The first result R1 is a result obtained by segmentation of the received data RD1 of the living body having the first attribute by the first training model 121. The first result R1 corresponds to the segmentation result of step S460. The second result R2 is a result obtained by segmentation of the received data RD1 by the second training model 122. The third result R3 is a result obtained by segmentation of the received data RD1 by a fourth training model (to be described later). The fourth result R4 is a result obtained by segmentation by the first training model 121 of the received data RD2 of the living body having the second attribute. The fifth result R5 is a result obtained by segmentation of the received data RD2 by the first training model 121. The fifth result R5 corresponds to the segmentation result of step S470. The sixth result R6 is a result obtained by segmentation of the received data RD2 by the fourth training model. FIG. 8 shows, as the segmentation results, the Dice coefficient and a schematic image in which the region of the muscle layer ML is masked in the same way as the thickness label LB in FIG. 4. The Dice coefficient represents the degree of overlap between the region of the muscle layer ML in the segmentation result of the received data and the region of the muscle layer ML in the thickness label LB associated with the received data. The correct answer ML1 in FIG. 8 schematically shows, in a manner similar to that of the thickness label LB in FIG. 4, a region to be identified as the muscle layer ML when segmentation was executed on the received data RD1. In substantially the same manner, the correct answer ML2 schematically shows a region to be specified as the muscle layer ML when segmentation was executed on the received data RD2.

The fourth training model is a training model different from the first training model 121 to the third training model 123. Specifically, the fourth training model is a training model that has been trained using the fourth training data as teaching data. The fourth training data is a dataset including a plural sets of first sample data SD1, the first thickness labels LB1 associated with the respective sets of the first sample data SD1, plural sets of second sample data SD2, and the second thickness labels LB2 associated with the respective sets of the second sample data SD2. In the fourth training model, the ratio of the first sample data SD1 to the sample data is smaller than that in the first training model 121. In the fourth training model, the ratio of the second sample data SD2 to the sample data is smaller than that in the second training model 122.

As illustrated in FIG. 8, among the segmentation results for the received data of the first attribute of the living body, from the first result R1 to the third result R3, the first result R1 had the highest Dice coefficient. This is because the main data of the first training data LD1 that was used for the training of the first training model 121 is the first sample data SD1. The Dice coefficient of the third result R3 is higher than the Dice coefficient of the second result R2. This is because the first sample data SD1 is not included in the second training data LD2 used for training of the second training model 122, while the first sample data SD1 is included in the fourth training data used for training of the fourth training model. However, due to the second sample data SD2 being included in the fourth training data, the feature quantity of the second sample data SD2, that is, the feature quantity caused by the second attribute being different from the first attribute, is more likely to be reflected in the training that uses the fourth training data than in training that uses the first training data LD1. On the other hand, in training that uses the first training data LD1, the feature quantity attributable to the first attribute is more likely to be reflected in the training. As a result, the Dice coefficient of the first result R1 is higher than the Dice coefficient of the third result R3.

Among the segmentation results for the received data RD2, the Dice coefficient of the fifth result R5 was the highest compared to the fourth result R4 and the sixth result R6. This is because the main data of the second training data LD2 is the second sample data SD2, substantially that same as the case of the first result R1 to the third result R3. The Dice coefficient of the sixth result R6 is higher than the Dice coefficient of the fourth result R4. This is because the second sample data SD2 is not included in the second training data LD2, whereas the second sample data SD2 is included in the fourth training data. However, due to the first sample data SD1 included in the fourth training data, the feature quantity caused by the first attribute different from the second attribute is more likely to be reflected in the training using the fourth training data than in the training using the second training data LD2. On the other hand, in the training using the second training data LD2, the feature amount caused by the second attribute is more likely to be reflected in the training. As a result, the Dice coefficient of the fifth result R5 is higher than the Dice coefficient of the sixth result R6. In this way, in the thickness calculating step in present embodiment, it is possible to more appropriately execute the segmentation of the target received data by using the calculation training model that has been trained by the teaching data corresponding to the attribute of the target living body TO. Since the thickness of the target tissue calculated using the result of appropriately executed segmentation, the thickness of the target tissue can be calculated with higher accuracy.

In step S480, the control device 100 controls the display section 150 to display the calculation result of the first process in step S460 or the second process in step S470 on the display section 150. In step S480, the display section 150 may display, for example, only the calculated thicknesses, or may display the segmentation result together with the thicknesses.

According to the thickness calculation method of the present embodiment described above, in the living body attribute classification step, the target living body TO is classified into one of the first attribute and the second attribute based on the target received data acquired in the data acquisition step. Then, in the thickness calculating step, the thickness of the target tissue is calculated by executing the first process when the target living body TO is classified into the first attribute and executing the second process when the target living body TO is classified into the second attribute. In the first process, the first training model 121 trained by the first training data LD1 corresponding to the first attribute is used, and in the second process, the second training model 122 trained by the second training data LD2 corresponding to the second attribute is used. In this way, the thickness of the target tissue is calculated using the target received data and the training model that has been trained using teaching data corresponding to the attribute of the target living body TO. Therefore, it is possible to increase the possibility that the thickness of the target tissue is calculated with higher accuracy.

In the present embodiment, the first attribute and the second attribute are attributes classified according to the size of the physique parameter. Therefore, in the living body attribute classification step, by acquiring the physique parameter based on the target received data, the target living body TO can be classified: of the first attribute and the second attribute. When preparing teaching data for training the first training model 121 or the second training model 122, sample data to be used as the teaching data can be classified according to the physique parameter. Therefore, it is possible to more easily prepare teaching data for training the first training model 121 and the second training model 122.

In the present embodiment, the physique parameter is a parameter representing fat thickness. Therefore, in the living body attribute classification step, by acquiring the parameter indicating the fat thickness on the basis of the target received data, it is possible to classify the living body TO of the target into one of the first attribute and the second attribute.

In the present embodiment, the thickness label LB is a label for specifying the positions of the first end Eg1 and the second end Eg2 in the thickness direction d1 of the target tissue. The processor 110 calculates the thickness of the target tissue in the thickness calculating step using the positions of the first end Eg1 and the second end Eg2 that were output by inputting the target received data. With this configuration, the calculation model can be generated as a training model for specifying the position of the first end Eg1 and the second end Eg2, and the thicknesses of the target tissue can be calculated by the calculation model using the specified position between the first end Eg1 and the second end Eg2. For example, as in the present embodiment, the first training model 121 or the second training model 122 can be generated as a training model for executing segmentation.

In the present embodiment, in the living body attribute classification step, the target living body TO is classified using the third training model 123 different from the first training model 121 and the second training model 122. In this way, in the living body attribute classification step, the target living body TO can be classified using the third training model 123, which is different from the calculation model. Therefore, for example, since a training model specialized for classification of the target living body TO can be used in the living body attribute classification step, it is possible to increase the possibility that the target living body TO is appropriately classified in the living body attribute classification step.

In the present embodiment, the third training model 123 was trained in advance using teaching data including the first sample data SD1, the physique label related to the physique parameter associated with the first sample data SD1, the second sample data SD2, and the physique label associated with the second sample data SD2. Therefore, regardless of whether the attribute of the target living body TO is the first attribute or the second attribute, the target living body TO can be appropriately classified in the living body attribute classification step. When preparing teaching data for training the third training model 123, sample data to be used as the teaching data can be classified according to the physique parameter. Therefore, it is possible to more easily prepare teaching data for training the third training model 123.

B. Other Embodiments (B-1) In the above embodiment, the first attribute and the second attribute are attributes classified according to the magnitude of the physique parameter. In contrast, the first attribute and the second attribute may not be such an attribute. For example, when the physique parameter is a vector quantity, the first attribute and the second attribute may be attributes classified in accordance with the direction of the physique parameter. In this case, the physique parameter may be, for example, a parameter represented by a multidimensional vector with various parameters such as fat thickness, body fat percentage, and BMI as components. In this case, the physique label may be a label associated with a parameter the represented by multidimensional vector.

(B-2) In the above embodiment, the physique parameter is a parameter representing fat thickness. In contrast, the physique parameter may not be a parameter representing fat thickness, and may be, for example, a parameter representing body fat percentage or BMI. Further, the physique parameter representing fat thickness, body fat percentage, or BMI may be, for example, a parameter represented by a multidimensional vector having any two or all of fat thickness, body fat percentage, and BMI as components. The physique parameter is not limited to the above, and may be a parameter relating to another physique. In this case, the physique label may be a label related to each parameter.

(B-3) In the above embodiment, the thickness label LB is a label that indicates each region included in the B-mode image of each sample data associated with the thickness label LB, and the region indicates any one of the fat layer FL, the muscle layer ML, or the internal organ OR. In contrast, for example, the thickness label LB may be a label that indicates whether each region included in the B-mode image of each sample data associated with the thickness label LB is a region representing the muscle layer ML or tissue other than the muscle layer ML. Even if the thickness label LB is such a label, the positions of the first end Eg1 and the second end Eg2 can be specified by the thickness label LB. In this case, when the target received data is input, the calculation model is generated as a training model for performing segmentation of two classes. The thickness label LB may not be a label for specifying the positions of the first end Eg1 and the second end Eg2 as long as it is a label relating to the thicknesses of the target tissues. In this case, for example, a value representing the thickness of the target tissue may be used as the thickness label LB.

(B-4) In the above embodiment, the third training model 123 is used in the living body attribute classification step. In contrast, the third training model 123 may not be used in the living body attribute classification step. In this case, in the living body attribute classification step, for example, the target living body TO may be classified by a rule-based model.

(B-5) In the above embodiment, the third training model 123 is a training model that was trained using the third training data LD3 as the teaching data. In contrast, the third training model 123 may not be such a training model, and may be, for example, a model similar to the fourth training model described in the first embodiment. Even in this case, since the first sample data SD1 and the second sample data SD2 are included in the fourth training data for training the fourth training model, it is possible to increase the possibility that the target living body TO is appropriately classified in the living body attribute classification step.

(B-6) In the above embodiment, the calculation device 20 includes the ultrasonic probe 410, but may not include the ultrasonic probe 410. In this case, the measurement data acquisition section 111 of the calculation device 20 may be configured to acquire the target received data transmitted from the ultrasonic probe 410, a computer, or a storage medium, provided outside the calculation device 20, for example.

(B-7) In the above embodiment, the received data is a B-mode image, but may not be a B-mode image. In this case, the received data may be, for example, a so-called A-mode data in which the amplitude of the reflected wave in the reception signal is represented for each distance.

(B-8) In the above embodiment, the first training model 121 and the second training model 122 are each a CNN, but may be a machine learning model other than a CNN. For example, the first training model 121 and the second training model 122 may be a vector neural network type machine learning model having a vector neuron layer, may be a recurrent neural network, or may be a machine learning model different from a neural network. Similarly, the third training model 123 may be a machine learning model other than the CNN.

(B-9) In the above embodiment, the calculation device 20 executes the first training process and the second training process but may not execute the first training process and the second training process. In this case, the first training model 121 and the second training model 122 may be generated outside the calculation device 20. In this case, the first training data LD1 and the second training data LD2 may not be stored in the storage device 120 of the calculation device 20. Similarly, the calculation device 20 may not execute the third training process. In this case, the third training data LD3 may not be stored in the storage device 120.

(B-10) In the above embodiment, the target tissue is a muscle layer. On the other hand, the target tissue may include other tissues in addition to or instead of the muscle layer. For example, the calculation device 20 may be configured to calculate the thickness of each of the muscle layer and the fat layer as the target tissue. For example, the target tissue may include two or more layers of muscle layers or two or more layers of fat layers.

(B-11) In the above embodiment, the target living body TO may be classified into three or more attributes in the living body attribute classification step. In this case, each training model corresponding to each of three or more attributes may be prepared, and in the thickness calculating step, the thickness of the target tissue may be calculated using the training model corresponding to the attribute of the target living body TO.

C. Other Aspects

The present disclosure is not limited to the above-described embodiments and can be implemented in various aspects without departing from the scope of the present disclosure. For example, the present disclosure can also be realized by the following aspects. The technical features in the above-described embodiment corresponding to the technical features in each aspect described below can be appropriately replaced or combined in order to solve a part or all of the problems of the present disclosure or in order to achieve a part or all of the effects of the present disclosure. In addition, if the technical features are not described as essential in this specification, the technical features can be appropriately deleted.

(1) According to a first aspect of the present disclosure, there is provided a thickness calculation method for calculating a thickness of the tissue in a living body by a computer. In this calculation method, the computer has a processor or a plurality of processors, and the processor or the plurality of processors performs a data acquisition step that acquires received data based on a reception signal output when an ultrasonic wave transmitted from an ultrasonic probe is reflected within a living body of a target and is received by the ultrasonic probe, a living body attribute classification step that classifies the living body of the target into one of a first attribute relating to a physique of the living body and a second attribute relating to the physique based on target received data, which is the received data acquired in the data acquisition step, and a thickness calculating step of (i) when the target living body is classified into the first attribute in the living body attribute classification step, calculating thickness of tissue at a predetermined part of the target living body by inputting the target received data into a first training model that learned in advance and (ii) when the target living body is classified into the second attribute in the living body attribute classification step, calculating the thickness of the tissue by inputting the target received data into a second training model that learned in advance. The first training model learned in advance using, as teaching data, first sample data, which is the received data for a biological sample having the first attribute, and a thickness label related to the thickness of the tissue associated with the first sample data. The second training model learned in advance using, as teaching data, second sample data that is the received data on the biological sample having the second attribute and the thickness label associated with the second sample data.

According to this aspect, the thickness of the tissue is calculated by using the target received data and the training model trained with the teaching data corresponding to the classified attribute of the living body of the target. Therefore, it is possible to increase the possibility that the thickness of the tissue is calculated with higher accuracy.

(2) In above-described aspect, the first attribute and the second attribute may be attributes classified according to the magnitude of a parameter related to the physique constitution. According to this aspect, in the living body attribute classification step, by acquiring the parameter related to physique, based on the target received data, the target living body can be classified into one of the first attribute and the second attribute.

(3) In the above-described aspect, the parameter may represent at least one of fat thickness, body fat percentage, or BMI. According to this aspect, in the living body attribute classification step, by acquiring the parameter indicated to fat thickness, body fat percentage, and BMI, based on the target received data, the target living body can be classified into one of the first attribute and the second attribute.

(4) In above-described aspect, the thickness label is a label that identifies positions of a first end and a second end in a thickness direction of the tissue, and in the thickness calculating step, the processor may calculate the thickness of the tissue using the positions of the first end and the second end, which are output by input of the target received data. According to this aspect, the calculation model can be generated as a training model for specifying the position the first end and the second end, and the thicknesses of the target tissue can be calculated using the specified position between the first end and the second end by the calculation model.

(5) In above-described aspect, in the living body attribute classification step, the target biological object may be classified into one of the first attribute and the second attribute by using a third training model different from the first training model and the second training model. According to this aspect, in the living body attribute classification step, the target living body can be classified using the third training model, which is different from the calculation model. Therefore, for example, since a training model specialized for classification of the target living body can be used in the living body attribute classification step, it is possible to increase the possibility that the target living body is appropriately classified.

(6) In above-described aspect, the first attribute and the second attribute are attributes classified according to the magnitude of a parameter related to the physique constitution and the third training model may learn in advance, as teaching data, the first sample data and a physique label related to the parameter associated with the first sample data, and the second sample data and a physique label associated with the second sample data. According to this aspect, regardless of whether the attribute of the target living body is the first attribute or the second attribute, the target living body can be appropriately classified in the living body attribute classification step.

(7) According to a second aspect of the present disclosure, there is provided a calculation device that calculates the thickness of the tissue in a living body. The calculation device includes a storage device that stores a first training model learned in advance and a second training model learned in advance, and a processor or a plurality of processors. the processor or the plurality of processors performs a data acquisition step that acquires received data based on a reception signal output when an ultrasonic wave transmitted from an ultrasonic probe is reflected within a living body of a target and is received by the ultrasonic probe, a living body attribute classification step that classifies the living body of the target into one of a first attribute relating to a physique of the living body and a second attribute relating to the physique based on target received data, which is the received data acquired in the data acquisition step, and a thickness calculating step of (i) when the target living body is classified into the first attribute in the living body attribute classification step, calculating thickness of tissue at a predetermined part of the target living body by inputting the target received data into a first training model and (ii) when the target living body is classified into the second attribute in the living body attribute classification step, calculating the thickness of the tissue by inputting the target received data into a second training model. The first training model learned in advance using, as teaching data, first sample data, which is the received data for a biological sample having the first attribute, and a label related to the thickness of the tissue associated with the first sample data. the second training model learned in advance using, as teaching data, second sample data, which is the received data on the biological sample having the second attribute and the label associated with the second sample data.

(8) In above-described second aspect, it may further include the ultrasonic probe that transmits ultrasonic waves to the living body of the target and that outputs the target received data.

(9) According to a third aspect of the present disclosure, there is provided a program for causing a computer to realize a function of calculating a thickness of the tissue in a living body. The program includes a function of executing a data acquisition step of acquiring received data based on a reception signal output when an ultrasonic wave transmitted from an ultrasonic probe is reflected in a living body of a target and is received by the ultrasonic probe, a function of executing a living body attribute classification step of classifying the target biological object into one of a first attribute relating to a physique of the biological object and a second attribute relating to the physique based on target received data, which is the data acquired in the data acquisition step, and a function of a thickness calculating step of (i) when the target living body is classified into the first attribute in the living body attribute classification step, calculating thickness of tissue at a predetermined part of the target living body by inputting the target received data into a first training model that learned in advance and (ii) when the target living body is classified into the second attribute in the living body attribute classification step, calculating the thickness of the tissue by inputting the target received data into a second training model that learned in advance. The first training model learned in advance using, as teaching data, first sample data, which is the received data for a biological sample having the first attribute, and a label related to the thickness of the tissue associated with the first sample data. The second training model learned in advance using, as teaching data, second sample data, which is the received data on the biological sample having the second attribute and the label associated with the second sample data.

In addition to the above aspects, the present disclosure can be implemented in aspects such as a method for generating a learning model, a program, a non-transitory storage medium in which a program is recorded, and a program product. The program product may be provided as, for example, a storage medium on which the program is recorded, or may be provided as a program product that can be distributed via a network.

What is claimed is:

1. A thickness calculating method for calculating a thickness of a target tissue in a target living body by a computer that includes a processor or a plurality of processors, the thickness calculating method comprising:

the processor or the plurality of processors performing:

a data acquisition step that acquires received data based on a reception signal output when an ultrasonic wave transmitted from an ultrasonic probe is reflected by the target tissue within the target living body and is received by the ultrasonic probe;

a living body attribute classification step that classifies the target living body into one of a first attribute relating to a physique of the target living body and a second attribute relating to the physique based on the acquired received data; and a thickness calculating step of (i) when the target living body is classified into the first attribute in the living body attribute classification step, calculating the thickness of the target tissue at a predetermined part of the target living body by inputting the acquired received data into a first training model that learned in advance and (ii) when the target living body is classified into the second attribute in the living body attribute classification step, calculating the thickness of the target tissue by inputting the acquired received data into a second training model that learned in advance, wherein the first training model learned in advance using, as teaching data, first sample data, the first sample data being data for a biological sample having the first attribute, and a thickness label related to a thickness of a tissue associated with the first sample data, the second training model learned in advance using, as teaching data, second sample data, the second sample data being data for a biological sample having the second attribute and a thickness label associated with the second sample data, each of the thickness label associated with the first sample data and the thickness label associated with the second sample data is a label that identifies, by segmentation of the acquired received data, positions of a first end and a second end in a thickness direction of the target tissue, the segmentation is a three-class segmentation that uses the label to indicate whether each pixel in the acquired received data represents one of a fat layer, a muscle layer, and an internal organ, the label specifies a boundary between the fat layer and the muscle layer and represents the first end and the second end, and in the thickness calculating step, the thickness of the target tissue is calculated using the positions of the first end and the second end, wherein the positions are output by input of the acquired received data.

2. The thickness calculating method according to claim 1, wherein the first attribute and the second attribute are attributes classified according to a magnitude of a parameter related to the physique.

3. The thickness calculating method according to claim 2, wherein the parameter represents at least one of a fat thickness, a body fat percentage, or a Body Mass Index (BMI).

4. The thickness calculation method according to claim 1, wherein in the living body attribute classification step, the target living body is classified into one of the first attribute or the second attribute by using a third training model different from the first training model and the second training model.

5. The thickness calculation method according to claim 4, wherein the first attribute and the second attribute are attributes classified according to magnitude of a parameter related to the physique, and the third training model learned in advance using, as teaching data, the first sample data and a physique label related to a parameter associated with the first sample data, and the second sample data and a physique label associated with the second sample data.

6. A calculation device for calculating a thickness of a target tissue in a target living body, the calculation device comprising:

a storage device for storing a first training model that was trained in advance and a second training model that was trained in advance; and a processor or a plurality of processors, wherein the processor or the plurality of processors performs:

a data acquisition step that acquires received data based on a reception signal output when an ultrasonic wave transmitted from an ultrasonic probe is reflected by the target tissue within the target living body and is received by the ultrasonic probe;

a living body attribute classification step that classifies the target living body into one of a first attribute relating to a physique of the target living body and a second attribute relating to the physique based on the acquired received data; and a thickness calculating step of (i) when the target living body is classified into the first attribute in the living body attribute classification step, calculating the thickness of the target tissue at a predetermined part of the target living body by inputting the acquired received data into the first training model and (ii) when the target living body is classified into the second attribute in the living body attribute classification step, calculating the thickness of the target tissue by inputting the acquired received data into the second training model, wherein the first training model learned in advance using, as teaching data, first sample data, the first sample data being data for a biological sample having the first attribute, and a label related to a thickness of a tissue associated with the first sample data, the second training model learned in advance using, as teaching data, second sample data, the second sample data being data for a biological sample having the second attribute and a label associated with the second sample data, each of the label associated with the first sample data and the label associated with the second sample data identifies, by segmentation of the acquired received data, positions of a first end and a second end in a thickness direction of the target tissue, the segmentation is a three-class segmentation that uses the label to indicate whether each pixel in the acquired received data represents one of a fat layer, a muscle layer, and an internal organ, the label specifies a boundary between the fat layer and the muscle layer and represents the first end and the second end, and in the thickness calculating step, the thickness of the target tissue is calculated using the positions of the first end and the second end, wherein the positions are output by input of the acquired received data.

7. The calculation device according to claim 6, further comprising:

the ultrasonic probe that transmits ultrasonic waves to the target living body and that outputs the acquired received data.

8. A non-transitory computer-readable storage medium storing a program, the program causing a computer to realize a function of calculating a thickness of a target tissue in a target living body, the program causing the computer to execute operations comprising:

executing a data acquisition step of acquiring received data based on a reception signal output when an ultrasonic wave transmitted from an ultrasonic probe is reflected by the target tissue within the target living body and is received by the ultrasonic probe;

executing a living body attribute classification step of classifying the target living body into one of a first attribute relating to a physique of the target living body and a second attribute relating to the physique based on the acquired received data; and executing a thickness calculating step of (i) when the target living body is classified into the first attribute in the living body attribute classification step, calculating the thickness of the target tissue at a predetermined part of the target living body by inputting the acquired received data into a first training model that learned in advance and (ii) when the target living body is classified into the second attribute in the living body attribute classification step, calculating the thickness of the target tissue by inputting the acquired received data into a second training model that learned in advance, wherein the first training model learned in advance using, as teaching data, first sample data, the first sample data being data for a biological sample having the first attribute, and a label related to a thickness of a tissue associated with the first sample data, the second training model learned in advance using, as teaching data, second sample data, the second sample data being data for a biological sample having the second attribute and a label associated with the second sample data, each of the label associated with the first sample data and the label associated with the second sample data identifies, by segmentation of the acquired received data, positions of a first end and a second end in a thickness direction of the target tissue, the segmentation is a three-class segmentation that uses the label to indicate whether each pixel in the acquired received data represents one of a fat layer, a muscle layer, and an internal organ, the label specifies a boundary between the fat layer and the muscle layer and represents the first end and the second end, and in the thickness calculating step, the thickness of the target tissue is calculated using the positions of the first end and the second end, wherein the positions are output by input of the acquired received data.

\* \* \* \* \*